United States Patent [19]
Chan

[11] Patent Number: 5,576,194
[45] Date of Patent: Nov. 19, 1996

[54] RECOMBINANT PROTEIN PRODUCTION

[75] Inventor: Sham Y. Chan, El Sobrante, Calif.

[73] Assignee: Bayer Corporation, West Haven, Conn.

[21] Appl. No.: 130,404

[22] Filed: Oct. 1, 1993

Related U.S. Application Data

[63] Continuation of Ser. No. 809,855, Dec. 18, 1991, abandoned, which is a continuation of Ser. No. 297,705, Jan. 13, 1989, abandoned, which is a continuation-in-part of Ser. No. 884,412, Jul. 11, 1986, abandoned.

[51] Int. Cl.$^6$ .................... C07K 14/755; C12N 5/02; C12N 5/10; C12N 15/12
[52] U.S. Cl. ............... 435/69.6; 435/240.1; 435/240.31; 530/383; 935/34
[58] Field of Search .................. 435/69.1, 69.6, 435/240.2, 240.31, 235.1, 320.1, 240.25; 530/350, 383; 935/34

[56] References Cited

U.S. PATENT DOCUMENTS 4,757,006  7/1988  Toole et al. .................. 435/69.6

FOREIGN PATENT DOCUMENTS 0201800  11/1986  European Pat. Off. .
8704187  7/1987  WIPO .

OTHER PUBLICATIONS

Truett et al DNA vol. 4, pp. 333–349 (1985).
Ill et al J. of Cellular Physiol. vol. 113, pp. 373–384 (1982).
Giguere et al Cancer Res. vol. 43, pp. 2121–2130 (1983).
Maciag et al Cell Bio International Reports, vol. 4, No. 1 Jan. 1980 pp. 43–50.
Kato et al J. Cellular Physiology vol. 120, pp. 354–363 (1984).
Schormuller, J. Lehrbuch der Lebensmittelchemie Springer–Verlag Berlin–Heidelberg, 1977 pp. 378–379.
Dorlington et al Somatic Cell Genetics vol. 8 pp. 403–412 (1982).
Miles Diagnostics Excyte Product Literature (1986).

*Primary Examiner*—Dian C. Jacobson
*Attorney, Agent, or Firm*—Sprung Horn Kramer & Woods

[57] ABSTRACT

Recombinant Factor VIII production is increased by supplementing the serum-free culture of mammalian host cells containing the gene therefor in a serum-free nutrient media with lipoprotein obtained from a mammalian source, preferably low density human lipoprotein or total bovine lipoprotein.

6 Claims, No Drawings

RECOMBINANT PROTEIN PRODUCTION

This application is a continuation of application Ser. No. 809,855, filed Dec. 18, 1991, now abandoned.

BACKGROUND OF THE INVENTION

Hemostasis is the primary mechanism whereby excessive extravascular blood loss is prevented by the formation of fibrin clots at the site of insult. The physiological mechanism by which these fibrin clots are formed is presently being elucidated. The evidence to date suggests that the clotting mechanism is attributed to a very complex activation cascade of various blood plasma factors each responsible for the sequential activation of the successive zymogen. Proper functioning of this cascade ultimately leads to the formation of fibrin and the cessation of blood loss.

Unfortunately, however, various disease states have been recognized which are attributable to metabolic errors within this blood coagulation cascade either due to a deficiency or total absence of one or more of the blood plasma factors. Chief among these disease states is classic hemophilia or simply hemophilia A. Hemophilia A is a hereditary X chromosome-linked recessive trait which is manifested by an absence of antihemophilic Factor A, which factor is designated by convention as Factor VIII. Therapeutic efforts for treating hemophilia A have focused on supplementing the blood of affected individuals by infusion with concentrates of Factor VIII in various pharmaceutical formulations. Such Factor VIII concentrates have, in the past, largely been prepared by cryoprecipitation of Factor VIII from blood plasma. However, owing to the minute amount of the factor in normal individuals, extremely large quantities of plasma must be processed in order to isolate quantities sufficient for therapy having activity levels adequate for administration in physiologically acceptable volumes of diluent.

With the advent of recombinant DNA technology and the promise of the expression of large quantities of proteins of medical importance (among others), the disadvantages of prior isolation and purification techniques for Factor VIII have become increasingly evident. Indeed, recent publications have reported the successful cloning and expression of the gene encoding Factor VIII (see infra). However, as can be appreciated, even with this technical accomplishment, certain limitations in the efficiency of the overall process may need to be overcome to optimize the benefits flowing from such technology. For example, in the specific case of Factor VIII produced by recombinant DNA techniques, the transformed host cell containing the gene encoding Factor VIII is cultured in a complex medium containing other serum proteins in high concentration. Thus, even after expression of the Factor VIII, recovery and purification of the factor from a culture supernatant containing a heterogeneous population of serum proteins still presents many technical problems. Such difficulties could be alleviated by a means of culturing the recombinant host in the absence of serum proteins in such a manner as to support cell growth without compromising the viability of the host and its ability to express and produce Factor VIII. The present invention is directed to such means and provides for the increased production of recombinant Factor VIII by culturing a host cell carrying a gene capable of directing the expression of Factor VIII in a serum-free nutrient medium supplemented with lipoprotein.

DESCRIPTION OF PERTINENT ART

The preparation of blood coagulation factors (particularly Factor VIII) by recombinant DNA techniques has been disclosed in various publications. For example, European Patent Application 160457 describes the production of functional human Factor VIII from the full DNA coding sequence thereof by genetic engineering methodologies. The Factor VIII is said to be produced in quantities sufficient to prove the identification and functionality thereof free of the contaminants with which it is normally associated in its non-recombinant cellular environment, such as vonWillebrand Factor. Similarly, PCT Application WO 85/01961 describes the identification and isolation of the porcine Factor VIII gene and the concomitant isolation and identification of the human Factor VIII gene by virtue of the homology between porcine and human Factor VIII. Also disclosed is the expression of porcine and human Factor VIII by recombinant DNA techniques using these genes. Likewise, European Patent Application 150735 is said to provide methods and compositions for the production of Factor VIIIc (including precursors and subunits thereof) by expression in a microorganism or mammalian tissue cell. UK Patent Application GB 2,125,409 discloses substantially the whole DNA sequence encoding Factor IX (the absence or deficiency of which is associated with Christmas disease) including the production thereof in a host such as *Escherichia coli*.

Maciag, T. et al, Cell Biology International Reports, Vol 4, No. 1, 43–49, disclose the culture of Baby hamster kidney cells in the complete absence of serum in a synthetic medium supplemented with insulin, transferrin, fibroblast growth factor and epidermal growth factor on cell culture dishes coated with fibronectin. No suggestion is made of supplementing the nutrient medium with lipoprotein. However, Giguere et al, Cancer Research 43, 2121–2130, May, 1983, disclose a proliferative response of nontransformed rat embryo cells and avian sarcoma virus-transformed B32 cells to high density lipoprotein (HDL), transferrin, insulin, epidermal growth factor and fibroblast growth factor in serum free media. Giguere et al state that nontransformed Rat-1 cells and transformed B31 cells grown in the presence of medium containing, respectively, HDL, transferrin, insulin, EGF, and dexamethasone or HDL, transferrin and insulin could be subcultured for more than 50 generations in the complete absence of serum without significant alteration in morphology, growth rate or tumorigenicity (B31 cells). In contrast, McClure et al in "Growth of Cells in Hormonally Defined Media" Ed. by Sato, GH, Pardee, AB, Sirbasku, DA, CSH Press, NY 1982, pp345–364, showed that transformed rat embryo cells showed a differential requirement to HDL to an extent that some transformants do not even survive in its absence while some transformants are independent of HDL for growth (p361, 3rd paragraph). It is evident that Giguere's findings cannot be generalized to other cell types.

The response of mammalian cells to human lipoproteins is unpredictable. Human lipoproteins have been reported to be cytotoxic to a number of mammalian cell lines (Apffel, C. A. 1976. Nonimmunological host defenses: A review. Cancer Res. 36:1527–1537; Prezioso, J. A. and P. H. Koo, 1987. Natural cytotoxins in human plasma: Isolation and characterization of phospholipids associated with cytotoxic lipoproteins. Molecular Toxicology 1:191–208). These findings further support the view that Giguere's conclusions cannot be extrapolated to other cell types.

The literature discloses various roles for lipoprotein in cell culture techniques. For example, in *J. Cell. Physiol.*, 113(3) pp. 373–384 (1982) the authors state that high density lipoprotein is an absolute requirement for the survival and growth of bovine adrenal cortical cells when maintained on an extracellular matrix. In *J. Cell. Physiol.*, 120 (3) pp. 354–363 (1984) low density primary cultures of rabbit costal chondrocytes proliferated on an extracellular matrix of corneal endothelial cells when the medium was supplemented with high density lipoprotein, transferrin, fibroblast growth factor, hydrocortisone and epidermal growth factor. Similarly, bovine lens epithelial cells when passaged to serum-free medium, proliferated actively on an extracellular matrix-coated dish when exposed to a mixture of Dulbecco's modified Eagle's medium supplemented with high density lipoprotein, transferrin, insulin and fibroblast growth factor (*Exp. Eye Res.*, 35 (3), pp. 259–270, 1982). The use of high density lipoprotein has been reported as a substitute for serum in the process of serially adapting the human mammary carcinoma cell line MCF-7 to grow in serum-free medium (*Biochem. Biophys. Res. Commun.*, 133 (1), pp. 105–112, 1985). Hence, it is known that in specific instances for particular cell lines, a high density lipoprotein-supplemented medium is needed to adapt a cell line to grow in a serum-free medium and may be needed for proliferation on an extracellular matrix. In either case, the effect of lipoprotein on a given cell culture is unpredictable. For example, in *Cell Struct. Funct.*, 8 (1), pp. 67–76 (1983), low density lipoprotein was said to promote the growth of human normal HEL cells and 4-nitroquinoline-1-oxide-transformed human fibroblast cells in the absence of serum. However, low density lipoprotein had no effect on the optimal growth of human fibroblast cells which were alpha-ray transformed.

None of the above-cited references either disclose or suggest the use of lipoprotein as taught herein. That is to say, the use of lipoprotein to effect the increased expression from cells of a transfected, heterologous gene has not been previously reported. Specifically, no such methodology has been applied to the production of recombinant Factor VIII.

SUMMARY OF THE INVENTION

The present invention is directed to a method for effecting the increased production of recombinant Factor VIII in a mammalian host cell carrying the gene therefor, comprising: culturing the mammalian host in a serum-free nutrient medium supplemented with mammalian lipoprotein so as to increase production of recombinant Factor VIII.

The lipoprotein, preferably total bovine lipoprotein or low density lipoprotein obtained from human serum or plasma, can be added before or after growth of the cells.

DETAILED DESCRIPTION OF THE INVENTION

As noted previously, techniques are available for the production of large quantities of protein by recombinant DNA techniques, which quantities have not been possible to obtain previously. Typically, the process for identifying and isolating the gene responsible for production of the protein follows a somewhat standard protocol. The protein of interest is first isolated from its naturally occurring environment and is extensively purified utilizing techniques such as immunoaffinity purification with a monoclonal antibody specific for the protein of interest. The amino acid sequence of the polypeptide may be determined by now conventional techniques and, based on the sequence information thus obtained, oligonucleotide probes may be prepared and used to identify and/or isolate the site of synthesis of the protein from the various tissues tested. Polyadenylated mRNA may then be isolated from the identified tissue which is then utilized to form single-stranded complementary DNA (cDNA) by the action of RNA-directed DNA polymerase (also referred to as "reverse transcriptase"). The reverse transcriptase products (either partial or complete copies of the mRNA template) typically exhibit short, partially double-stranded hairpin loops at their 3' termini which act as primers for DNA polymerase. The DNA polymerase requires the presence of a DNA strand having a free 3'-hydroxyl group to which new nucleotide residues are added, thereby extending the chain in a 5' to 3' direction. The resulting double-stranded cDNA is then treated with S1 nuclease to remove a residual single strand fragment thereby generating a "blunt-end" duplex DNA segment. Other procedures for producing cDNA libraries are available. See, for example, Chan and Whitted in *Developments in Industrial Microbiology*, Vol. 9, pages 171–180 (1985), which is incorporated herein by reference. The DNA segment encoding the protein of interest is then ligated into an appropriate vector for subsequent transformation of a suitable host to create an expression system which directs the synthesis of the desired product.

The general procedures alluded to above are described in greater detail in *Molecular Cloning, A Laboratory Manual*, Maniatis et al, Cold Spring Harbor Laboratory, 1982 which is incorporated herein by reference. Details of the above-procedures as they specifically relate to the production of recombinant Factor VIII may be obtained from the following (each of which are expressly incorporated herein by reference): European Patent Application 160457; PCT Application Number PCT/US84/01641, published as WO 85/01961; European Patent Application 157556; and European Patent Application 150735. Thus, as used herein, the term "recombinant Factor VIII" refers to that functional protein that is produced by molecular biological techniques as outlined above which protein is capable of correcting human Factor VIII deficiencies.

The method disclosed and claimed herein provides for increased production of recombinant Factor VIII from mammalian host cells carrying the gene therefor. The phrase "increased production" as used herein is defined as production to greater extent than that possible in a recombinant system which does not utilize lipoprotein and serum-free conditions. By "serum-free" is meant culturing the host cells carrying the gene for Factor VIII in the essential absence of serum. While it is preferable to carry out the method of the present invention in the absence of serum, the presence of minor amounts of serum which do not deleteriously affect the yield of Factor VIII are clearly contemplated as falling within the scope of the present invention. However, as can be appreciated by the skilled artisan, the presence of increasing amounts of serum in the nutrient medium renders more difficult the purification of Factor VIII from the increased population of heterogeneous proteins present in serum.

Host cells suitable for Factor VIII expression may in general be derived from multicellular organisms. Mammalian cells such as VERO and HeLa cells, human kidney cells, Chinese hamster ovary (CHO) cells, baby hamster kidney (BHK) cells, W-138, COS-7 and MDCK cell lines are preferred. Particularly preferred are baby hamster kidney cells, specifically those transfected with a gene capable of directing the expression of Factor VIII as described in European Patent Application 160457 (including derivatives such as clonal variants and progeny thereof). Such a cell line has been deposited with the American Type Culture Collection and has been assigned the accession number ATCC CRL-8544.

The desired host cell line carrying the gene encoding Factor VIII is cultured by conventional techniques through the growth phase thereof in an appropriate medium containing typical amounts of serum (i.e., anywhere from about 7 to about 10 percent). The serum is maintained in the medium until the cells reach confluency and the maintenance phase of the cell cycle begins. This procedure is standard in the art. However, at the approximate point where the culture reaches the maintenance phase of the cell cycle (i.e., when the cells reach confluency) the spent nutrient medium containing the serum is replaced with a serum-free nutrient medium supplemented with lipoprotein and the culture is allowed to continue in the maintenance phase. Factor VIII is then recovered from each harvest when indicated. The skilled artisan will appreciate that the serum-free conditions (supplemented with lipoprotein) under which the maintenance phase of the culture is conducted, allows for a greatly facilitated purification of the Factor VIII from the spent nutrient medium than if serum proteins are present. It will be further appreciated that the presence of lipoprotein in the nutrient medium not only effects the increased production of Factor VIII from the host cell (as compared to culturing under serum supplemented conditions), but also sustains the viability of the cells for a prolonged period thus making increased numbers of harvests of Factor VIII possible.

The nutrient medium chosen for culturing the host cell line is not critical to the present invention and may be any one of, or combination, of those known to the art which are suitable for the selected host cell line. Illustrative of such media are Dulbecco's Modified Eagle Medium, Eagle's Minimum Essential Medium, Eagle's Basal Medium, Ham's Medium F-10, Ham's Medium F-12, RPMI-1640 Medium, and the like. All such media are commercially available from sources such as Sigma Chemical Company, GIBCO and M.A. Bioproducts, for example. The nutrient media may also contain Various buffers such as HEPES (N-2-hydroxyethylpiperazine-N'-2-ethanesulfonic acid) and may also be supplemented with factors such as insulin, transferrin, testosterone, sodium selenite, ethanolamine, glutamine, saturated and unsaturated fatty acids and the like in addition to the lipoprotein. The amounts of such factors added to the nutrient medium are conventional in the art. For example, the quantity of insulin may range from about 5 to about 10 micrograms per milliliter (µg/ml) of nutrient medium; the quantity of transferrin may range from about 2.5 to about 25 µg/ml of nutrient medium; the quantity of glutamine may range from about 200 to about 600 µg/ml of nutrient medium; saturated and unsaturated fatty acids may range from about 1 to about 10 µg/ml of nutrient medium; and the quantity of testosterone may range from about 10 to about 50 nanograms (ng) per milliliter of nutrient medium.

The lipoprotein which is used to supplement the nutrient media may be of any origin although mammalian sources such as cow, horse, sheep, pig or man are preferred. The lipoprotein is present in the nutrient medium in an amount capable of continuing the viability of the cells during the maintenance phase of the life cycle of the host cells. These lipoproteins are isolated from the serum or plasma of the mammalian host. Preferably, it has been found that this amount varies from 0.1 mg/ml to 2.0 mg/ml of nutrient medium. Particularly preferred are total bovine lipoprotein and low density human lipoprotein.

The total bovine lipoprotein is used synonymously with bovine lipoprotein herein. Although results indicate that any class of bovine lipoprotein will function as claimed in this invention, bovine lipoprotein is approximately 80% high density lipoprotein. Since it is impracticable to separate the classes, the total isolated bovine lipoprotein is conveniently used. Bovine lipoprotein is commercially available from various sources such as Pentex Lipoprotein Solution (Catalog No. 82-004) and Pentex Lipoprotein Cholesterol Solution (Catalog No. 82-108), both of which are available from Miles Inc., Elkhart, Ind. Bovine lipoprotein can also be prepared by ultra-centrifugal flotation of freshly isolated bovine serum using standard techniques as described, infra. Particularly preferred is a total bovine lipoprotein content of from 0.2 mg/ml to 1.0 mg/ml of nutrient medium.

Low density lipoprotein from human serum or plasma is also useful in this invention. Low density human lipoprotein is added to the nutrient medium during the maintenance phase of the life cycle of the host cells. Preferably, it has been found that this amount varies from about 0.05 mg/ml to 0.25 mg/ml of nutrient medium. It has been found that high density lipoprotein actually inhibits the production of Factor VIII. Various classes of human lipoproteins can be prepared by standard sequential ultracentrifugal flotation techniques (see, for example, Hayel, R. J., H. S. Edger and J. H. Bvagdon, 1955, The distribution and chemical composition of ultracentrifugally separated lipoproteins in human serum. J. Clinical Invest., 34:1345–1353) or can be purchased from Sigma Co.

In addition to conventional techniques such as roller bottle culturing, the method of the present invention is also applicable for use with micro-carrier systems such as described in *Methods in Enzymology*, Vol. LVIII, "Cell Culture" (1979), W. B. Jakoby and I. H. Pastan, Editors (which is incorporated herein by reference). Suitable micro-carriers include, for example, the various Cytodex microcarriers (i.e., Cytodex-1, Cytodex-2, Cytodex-3, available from Pharmacia, Inc.), Gelibeads (available from K. C. Biologicals), and the like. Further, the method of the present invention is also applicable to cell suspension systems. Particularly preferred is a bovine lipoprotein content of from about 0.2 mg/ml to 0.4 mg/ml of nutrient medium for stationary culture and from about 1 mg/ml to 2 mg/ml of nutrient medium for suspension or microcarrier culture.

The culture conditions are chosen with respect to standard considerations for the cell line being used. Suffice it to say that the chosen cell line carrying the gene capable of directing the expression of Factor VIII may be grown under such temperatures and for such time in a serum-free nutrient medium supplemented with lipoprotein as may be sufficient to effect the increased production of recombinant Factor VIII from the host. For example, for mammalian cell lines it may be desirable to conduct the culture at a temperature of from about 36° to 38° C. for about 24 to about 72 hours. However, selection of these parameters is routine and well within the skill of the artisan. Following culturing of the host cell, the Factor VIII may be recovered from the spent nutrient medium by standard methodologies such as centrifugation or ultrafiltration. If desired and/or necessary, the recovered Factor VIII may be purified by, for example, ion exchange or size exclusion chromatography, immunopurification, and the like.

The following examples are provided as a means of illustrating the present invention and are not to be construed as limiting the invention which is solely defined by the claims.

EXAMPLE 1

Bovine lipoprotein suitable for use in the present invention may be prepared as follows. To 50 ml of fresh bovine serum (obtained from a commercial slaughterhouse) was added 16 grams (g) of potassium bromide so as to adjust the density of the bovine serum to 1.21 g/ml. The serum was then centrifuged at 40,000 revolutions per minute (rpm) for 24 hours at 4° C. in an ultracentrifuge (a Beckman Ti45 being preferable) resulting in a separation of phases. The top, yellow, oily lipoprotein fraction was then collected and again centrifuged at 40,000 rpm for 24 hours. The lipoprotein fraction was isolated and dialyzed extensively against NaCl:EDTA (0.15 millimolar NaCl, 1.0 millimolar EDTA, pH 7.4). The dialyzed lipoprotein was then sterilized using a 0.2μ filter (Millipore). If desired, the lipoprotein may be quantified by a Bradford assay kit (commercially available from Biorad, Inc. under catalog Number 500-0002) and the cholesterol content may be quantified using a kit available from Sigma Chemical Co. (catalog number 351-20).

EXAMPLE 2

Baby hamster kidney cells (BHK-21) transfected with a gene capable of directing the expression of Factor VIII were obtained from Genentech, Inc., South San Francisco, Calif., U.S.A. The cell line was prepared as described in detail in European Patent Application 160457, and was deposited with the American Type Culture Collection and given accession number ATCC CRL-8544.

The BHK-21 cells containing the gene encoding Factor VIII were grown to confluency (as described in detail in the above-noted European Patent Application 160457) and were subsequently trypsinized with 0.25% trypsin-EDTA (commercially available from GIBCO). The cells were then washed with Hank's balanced salt solution (HBSS) and counted under a microscope using a hemocytometer. 20×10$^6$ cells were seeded into a 490 centimeter (cm)$^2$ roller bottle (Corning Glass, Inc.) to which was added 150 ml of growth medium containing Ham's Medium F-12 and Dulbecco's (low glucose) Minimum Essential Medium (50:50, by weight) and 7% fetal bovine serum. The cells were allowed to grow at 37° C. for 72 hours at a roller speed of 0.3 rpm. After the cells reached confluency, the spent media was decanted and discarded and the cells were washed with 100 ml of HBSS. A serum-free nutrient medium was then prepared and contained the following: Ham's Medium F-12 and Dulbecco's (low glucose) Minimum Essential Medium (50:50, by weight), bovine lipoprotein as prepared in Example 1 (0.4 mg/ml), bovine insulin (5.0 μg/ml), bovine transferrin (2.5 μg/ml) glutamine (292 μg/ml) and MgCl$_2$ (15 millimolar).

100 ml of this serum-free nutrient medium was then added to the cells which were allowed to grow at 37° C. for 48 hours at a roller speed of 0.3 rpm. The spent serum-free nutrient medium was then harvested for Factor VIII and 100 ml of fresh serum-free nutrient medium was added to the cells and again allowed to grow at 37° C. for 48 hours at a roller speed of 0.3 rpm. This process was repeated until 3 harvests of spent serum-free nutrient medium containing recombinant Factor VIII were obtained. Each harvest was individually assayed for Factor VIII activity using a chromogenic substrate determination method. The assay is sold commercially as a test kit known as Coatest Factor VIII and is available from Helena Laboratories, Beaumont, Tex. U.S.A. (Catalog No. 5293). The procedures for use are provided by the manufacturer and are further elaborated in European Patent Application 160457. The Factor VIII activity for each of the three harvests as determined with the Coatest Factor VIII kit are set forth in Table I.

TABLE I

| Harvest No. | Factor VIII Activity (units/liter)[a] |
|---|---|
| 1 | 250 |
| 2 | 210 |
| 3 | 220 |

[a]One unit of Factor VIII activity is defined as that activity present in one milliliter of human plasma As can be seen from the data presented in Table I, culturing the BHK-21 cells containing the gene encoding Factor VIII under serum-free conditions supplemented with bovine lipoprotein resulted in an elevated production of Factor VIII. By comparison, the use of conventional serum-containing nutrient medium, not supplemented with lipoprotein, to culture the above-described BHK-21 cell line (i.e., ATCC CRL-8544), produced Factor VIII in a quantity of from about 150 to about 200 units/liter. Further, cells not grown under serum-free conditions typically died after the second harvest.

EXAMPLE 3

A clonal variant of the BHK-21 cell line described in Example 2 (i.e., a clonal variant of ATCC CRL-8544) was obtained from Genentech, Inc., South San Francisco, Calif., U.S.A. Utilizing the procedures described in Example 2, the clonal variant was cultured under serum-free conditions supplemented with bovine lipoprotein through five harvests. These data are shown in Table II.

TABLE II

| Harvest No. | Factor VIII Activity (units/liter)[a] |
|---|---|
| 1 | 1500 |
| 2 | 1850 |
| 3 | 2840 |
| 4 | 3620 |
| 5 | 1750 |

[a]One unit of Factor VIII activity is defined as that activity present in one milliliter of human plasma As can be seen from the data presented in Table II, culturing the clonal variant of the BHK-21 cells containing the gene encoding Factor VIII under serum-free conditions supplemented with lipoprotein resulted in significantly elevated production of Factor VIII. By Comparison, the use of conventional serum-containing nutrient medium not supplemented with lipoprotein, produced Factor VIII in a quantity of from about 800 to about 1200 units/liter (for the clonal variant). Further, cells not grown under serum-free conditions typically detached and died after the second harvest.

EXAMPLE 4

In order to show that the method of the present invention is also applicable to the production of recombinant Factor VIII utilizing a microcarrier system, the following was conducted.

1 gm of Cytodex-3 microcarriers (Pharmacia, Inc.) were washed and hydrated in 500 ml of phosphate buffered saline (GIBCO) for 4 hours after which the microcarriers were autoclaved at 121° C. for 30 minutes. The microcarriers were washed twice in 250 ml of a growth medium containing equal parts (by weight) of Ham's F-12 Medium and Dulbecco's Modified Eagle Medium and were then suspended in 250 ml of the growth medium supplemented with 7% fetal bovine serum in a Bellco microcarrier spinner flask (Bellco Glass, Inc.). 40×10⁶ BHK-21 cells transfected with a gene capable of directing the expression of Factor VIII (as described in Example 3) were added to the microcarriers. The resulting cell suspension was incubated at 37° C. for 3 hours with intermittent stirring (at 30 rpm for 2 minutes at 30 minute intervals) after which an additional 250 ml of the above-described growth medium supplemented with 7% fetal bovine serum was added. The microcarriers were then incubated at 37° C. under continuous stirring at 30 rpm. After 72 hours, the spent medium was removed and the microcarriers were washed twice with HBSS. 500 ml of the serum-free nutrient medium, composed as described in Example 2, was added to the microcarriers and the system was allowed to incubate at 37° C. with continuous stirring (30 rpm). At 24 hour intervals the serum-free nutrient medium was harvested and replaced in the microcarrier system with 500 ml of fresh serum-free nutrient medium. The culture was terminated at day 9 with a total of 6 harvests of spent serum-free nutrient medium containing recombinant Factor VIII. Each harvest was individually assayed for Factor VIII activity using the chromogenic substrate determination method discussed in Example 2. The data are shown in Table III.

TABLE III

| Harvest No. | Factor VIII Activity (units/liter)[a] |
| --- | --- |
| 1 | 395 |
| 2 | 368 |
| 3 | 620 |
| 4 | 874 |
| 5 | 643 |
| 6 | 979 |

[a]One unit of Factor VIII activity is defined as that activity present in one milliliter of human plasma.

As can be seen from the data presented in Table III, by utilizing a microcarrier system to culture the BHK-21 cells containing the gene encoding Factor VIII under serum-free conditions supplemented with lipoprotein, a significantly elevated production of Factor VIII was achieved. By comparison, the use of conventional serum-containing nutrient medium not supplemented with lipoprotein in a microcarrier system, produced Factor VIII in a quantity of from about 200 to about 300 units/liter. Further, while only six harvests were made in this particular instance, the skilled artisan can appreciate that additional harvests may be made (typically as many as 10 to about 15) since the viability of the cells is maintained to a greater extent.

EXAMPLE 5

Factor VIII was produced by culturing human kidney cells containing the gene encoding fusion Factor VIII under serum-free production. Production conditions were similar to those used for baby hamster kidney cells. A description of the derivation of this expression host is found in Biochemistry 25:8384–8347. The cells were grown in serum containing media until confluency was reached. The cells were then switched to serum-free production median with or without bovine lipoprotein as shown in Table IV. Harvests were done at 48 hour intervals.

TABLE IV

Production of fusion Factor VIII in human kidney cells grown in roller bottles using bovine lipoprotein as a supplement.

| Conditions | Units/liter | | | | |
| --- | --- | --- | --- | --- | --- |
|  | Harvest 1 | 2 | 3 | 4 | 5 |
| Lipoprotein | | | | | |
| 0.4 mg/ml | 15,400 | 28,800 | 50,300 | 28,000 | 18,000 |
| 0.2 | 15,000 | 22,000 | 38,000 | 27,000 | 11,000 |
| 0 | 4,000 | 3,000 | 5,000 | 3,000 | 2500 |

EXAMPLE 6

Factor VIII was produced on microcarriers by culturing kidney cells containing the gene encoding Factor VIII, derived as shown in Biochemistry 25:8343–8347. The production conditions were similar to those used for baby hamster kidney cells in the previous Example 5 except a high glucose medium was used. (High glucose medium is defined as containing about 4.5 mg glucose/ml medium.) Data from the experiments, indicating increased production of Factor VIII with the addition of bovine lipoprotein, are shown in Table V.

TABLE V

Production of fusion Factor VIII from human kidney cells grown on microcarriers.

| Conditions | Units/liter | | | |
| --- | --- | --- | --- | --- |
|  | Harvest 1 | 2 | 3 | 4 |
| Lipoprotein | | | | |
| 1 mg/ml | 25,000 | 30,000 | 40,000 | 30,000 |
| 0 | 3,000 | 2500 | 2,000 | 1,000 |

EXAMPLE 7

The effect of supplementing serum-free nutrient media with different classes of human lipoprotein (very low density lipoprotein, VLDL; low density lipoprotein, LDL; and high density lipoprotein, HDL) was investigated. The experiment was done in 12 well plates, essentially a production experiment done micro-scale, to screen agents. The results showed that low density lipoprotein is responsible for enhancing Factor VIII production in human kidney cells. The data (shown in Table VI) also showed that high density lipoprotein inhibits production of Factor VIII from these cells.

TABLE VI

Effect of human lipoprotein on the production of fusion Factor VIII in human kidney cells.

| Conditions | Units/liter |
| --- | --- |
| VLDL | |
| 0.05 mg/ml | 2400 |
| 0.20 | 1680 |
| LDL | |
| 0.05 | 4200 |
| 0.20 | 6000 |

TABLE VI-continued

Effect of human lipoprotein on the production of fusion Factor VIII in human kidney cells.

| Conditions | Units/liter |
|---|---|
| HDL | |
| 0.05 | 1200 |
| 0.20 | 690 |
| Without lipoprotein | 2700 |

The data indicate that the effective dose range of human LDL is 0.05 to 0.25 mg/ml.

EXAMPLE 8

Factor VIII was produced under serum-free conditions in Chinese hamster ovary (CHO) cells containing the gene encoding Factor VIII with the use of bovine lipoprotein as a supplement. Conditions used were similar to those in Example 7. The data shown in Table VII indicates the increased production of Factor VIII with the addition of bovine lipoprotein. The most preferred range of bovine lipoprotein addition is from about 0.2 to 0.5 mg/ml.

TABLE VII

Effect of lipoprotein on the production of Factor VIII in Chinese hamster ovary cells.

| Conditions | Units/liter |
|---|---|
| Bovine lipoprotein | |
| 0.20 mg/ml | 180 |
| 0.5 | 200 |
| 1.0 | 140 |
| 0 | 70 |

It is understood that many modifications and variations can be made without departing from the spirit and scope of the invention, which is solely defined by the claims.

What is claimed is:

1. A method for expressing recombinant Factor VIII in a mammalian host cell carrying the gene therefor, said method comprising culturing said mammalian host cell in a serum-free nutrient medium supplemented with insulin, transferrin and total bovine lipoprotein, wherein said mammalian host cell is selected from the group consisting of baby hamster kidney cells, human kidney cells and Chinese hamster ovary cells, and wherein the amount of said total bovine lipoprotein in said nutrient medium is from about 0.2 mg/ml to about 1.0 mg/ml.

2. The method of claim 1 wherein the amount of said bovine lipoprotein present in the nutrient medium is from 0.2 mg/ml to 0.5 mg/ml.

3. The method of claim 1 wherein the amount of said bovine lipoprotein present in the nutrient medium is from 0.2 mg/ml to 0.4 mg/ml for stationary culture.

4. The method of claim 1 wherein the amount of said bovine lipoprotein present in the nutrient medium is about 1 mg/ml for suspension or microcarrier culture.

5. A method for expressing recombinant Factor VII from a baby hamster kidney host cell line deposited with the American Type Culture Collection and given accession number ATCC CRL 8544, comprising: culturing said host cell in a serum-free nutrient medium supplemented with insulin, transferrin and total bovine lipoprotein, wherein the amount of said total bovine lipoprotein in said nutrient medium is from about 0.2 mg/ml to about 1 mg/ml.

6. A method for expressing recombinant Factor VIII from a baby hamster kidney host cell line deposited with the American Type Culture Collection and given accession number ATCC CRL 8544, comprising: growing said host cell in a serum-free nutrient medium supplemented with insulin and transferrin and adding, after growth, total bovine lipoprotein, wherein the amount of said total bovine lipoprotein added is from about 0.2 mg/ml to about 1 mg/ml.

* * * * *

UNITED STATES PATENT AND TRADEMARK OFFICE
CERTIFICATE OF CORRECTION

PATENT NO. : 5,576,194
DATED : November 19, 1996
INVENTOR(S) : Chan, Sham Y.

It is certified that error appears in the above-indentified patent and that said Letters Patent is hereby corrected as shown below:

Col. 12, line 23   Delete Factor " VII " and substitute -- VIII --

Signed and Sealed this

Twenty-first Day of April, 1998

Attest:

BRUCE LEHMAN

Attesting Officer   Commissioner of Patents and Trademarks